United States Patent [19]

Bireley et al.

[11] Patent Number: 4,657,039

[45] Date of Patent: Apr. 14, 1987

[54] MOISTURE SENSOR

[75] Inventors: Richard L. Bireley, San Diego; Rumult Iltis, La Jolla, both of Calif.

[73] Assignee: Ranya L. Alexander, San Diego, Calif.

[21] Appl. No.: 646,641

[22] Filed: Aug. 30, 1984

[51] Int. Cl.[4] .............................................. A01G 25/16
[52] U.S. Cl. .............................. 137/78.3; 137/624.11; 340/604; 361/178; 361/196; 239/64
[58] Field of Search ............... 361/178, 203, 195, 196; 239/63, 64–65; 137/78.3, 624.11; 340/604

[56] References Cited

U.S. PATENT DOCUMENTS

| | | | |
|---|---|---|---|
| 3,418,571 | 12/1968 | Isoda et al. | 324/61 QL |
| 3,689,907 | 9/1972 | Guajardo | 361/178 |
| 3,771,548 | 11/1973 | Rauchwergen | 137/392 |
| 3,824,460 | 7/1974 | Gustafson | 324/61 R |
| 3,874,590 | 4/1975 | Gibson | 239/63 |
| 3,882,381 | 5/1975 | Gregory | 324/61 R |
| 3,882,383 | 5/1975 | Matlin | 324/65 R |
| 3,968,428 | 7/1976 | Numoto | 324/65 R |
| 3,991,375 | 11/1976 | Riggs et al. | 239/64 |
| 4,012,673 | 3/1977 | Saarem et al. | 137/624.11 |
| 4,029,959 | 6/1977 | Cottingham et al. | 250/239 |
| 4,040,436 | 8/1977 | Caldwell | 137/1 |
| 4,122,389 | 10/1978 | Haagen | 324/65 R |
| 4,137,931 | 2/1979 | Hasenbeck | 73/73 |
| 4,180,087 | 12/1979 | Meisner et al. | 137/624.11 |
| 4,197,866 | 4/1980 | Neal | 239/63 |
| 4,204,106 | 5/1980 | Colten | 219/213 |
| 4,216,789 | 8/1980 | Hasenbeck | 239/63 |
| 4,333,490 | 6/1982 | Engler, Sr. | 137/78.3 |
| 4,341,112 | 7/1982 | Mackay et al. | 73/73 |
| 4,514,722 | 4/1985 | Butcheler et al. | 340/604 |

Primary Examiner—A. Michael Chambers
Attorney, Agent, or Firm—Baker, Maxham & Jester

[57] ABSTRACT

A moisture sensor having an oscillator circuit with its output frequency directly proportional to moisture percentage present in the substance of interest. The oscillator circuit includes two spaced plates in the substance and functioning as a capacitor. The frequency of the oscillations changes as the capacitance between the plates changes due to the moisture present between the plates. The sensor is particularly adapted for use as a soil moisture detector and provides indications of wet or dry conditions.

16 Claims, 4 Drawing Figures

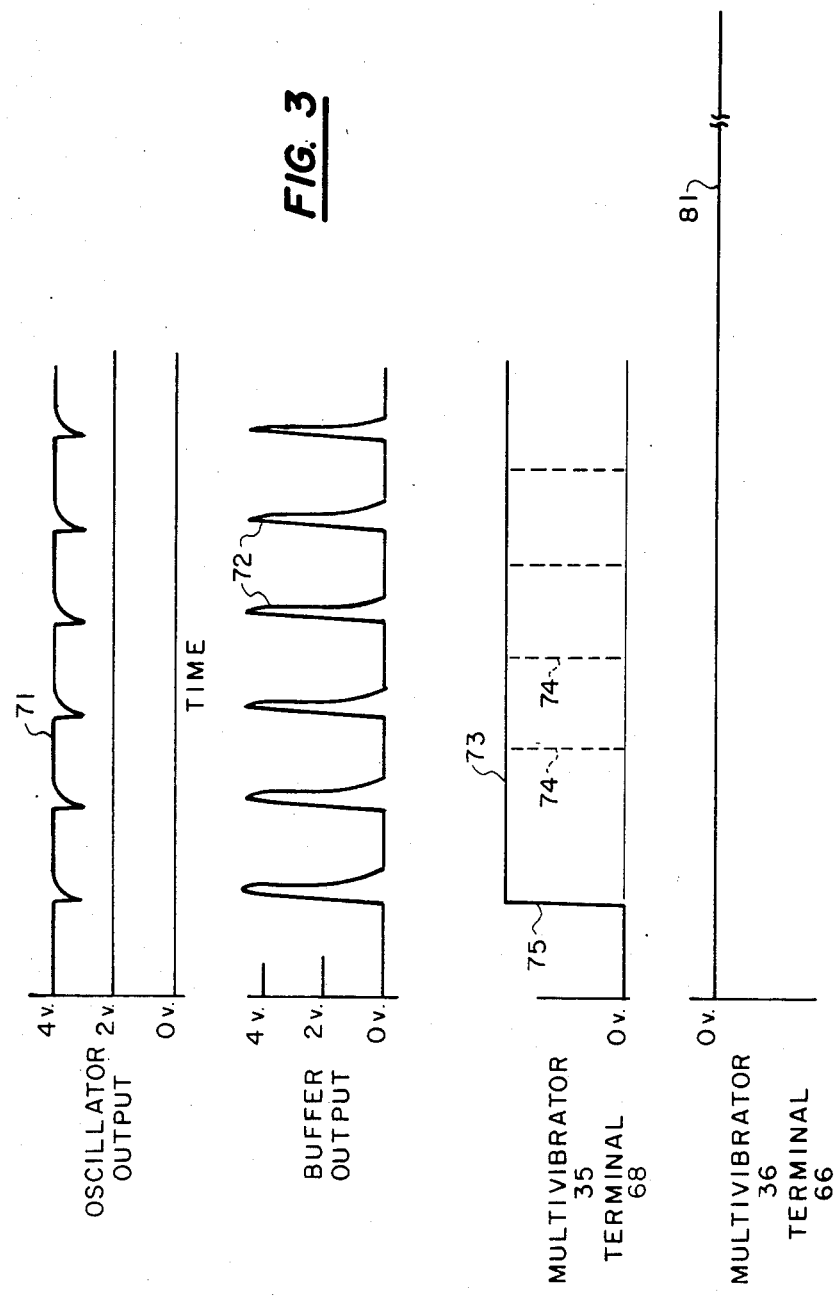

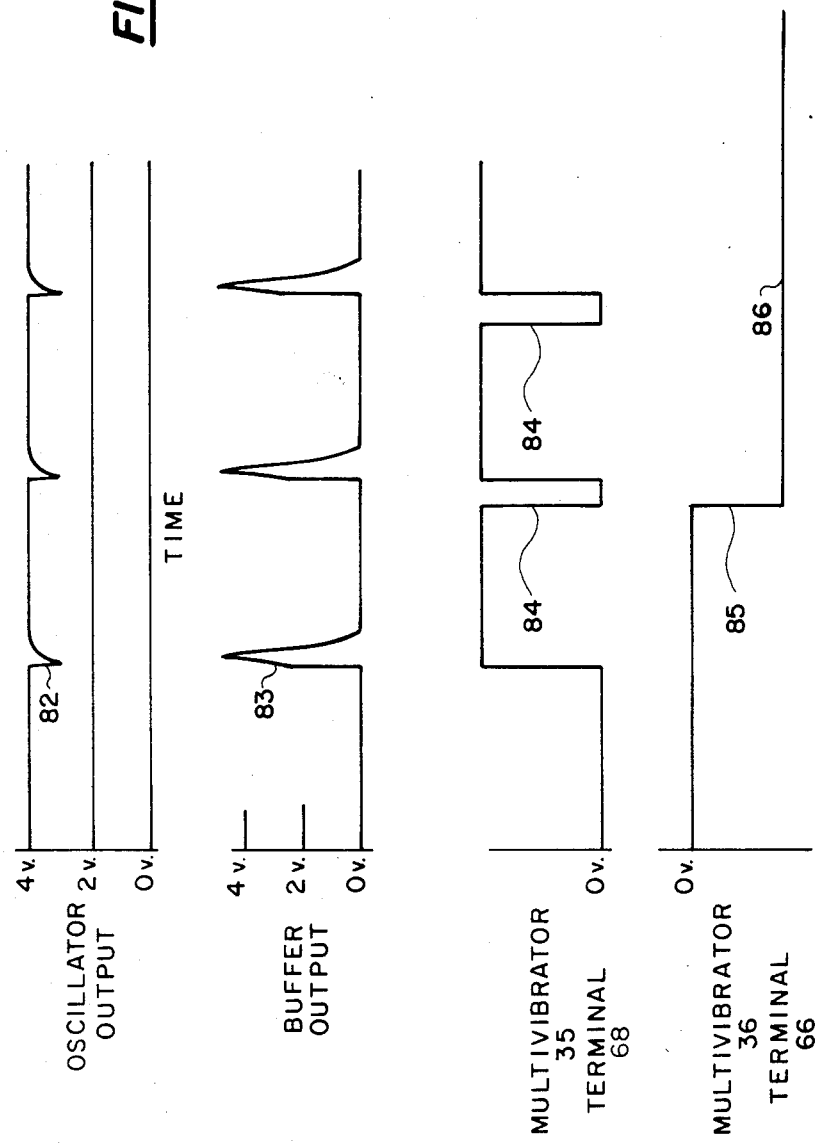

MOISTURE SENSOR

FIELD OF THE INVENTION

This invention relates generally to moisture sensors and more particularly to a moisture sensor having an oscillator with a frequency varying with moisture percentage.

BACKGROUND OF THE INVENTION

Lawn watering is generally anything but a precise process. Many people water when the lawn looks dry or when they think of it. Alternatively, a watering system may be on a timer whereby the lawn is watered at timed intervals, irrespective of whether or not it needs watering.

Apparatus to determine moisture content in various substances have been available in different forms and with varying degrees of success. However, a simple, inexpensive and practical system for sensing moisture percentage in media such as earth, in order to provide indications which may be adapted for controlling a lawn watering system, has not previously been available.

SUMMARY OF THE INVENTION

Broadly speaking, this invention relates to a moisture sensor and more particularly to such a sensor for a lawn watering system where the extent of watering is based on the percentage of moisture in the soil.

The system comprises a variable oscillator, the frequency of which is dependent on the capacitance between two spaced plates buried in the soil and connected in the oscillator circuit. The output of the oscillator is coupled through a buffer to a timing circuit which in turn controls the sprinkler solenoid. The system employs the standard 24 volt AC power system present in most lawn watering systems, and the solenoid of those systems.

The moisture sensor system of this invention can be easily calibrated to accomodate the particular areas of the capacitive sensor plates and the distance between them. Further, the system can be calibrated to commence watering when the moisture level in the soil reaches a predetermined low level, and to turn off the watering system when the moisture in the soil reaches a predetermined higher level.

BRIEF DESCRIPTION OF THE DRAWING

The objects, advantages and features of this invention will be more readily appreciated from the following detailed description when read in conjunction with the accompanying drawing, in which:

FIG. 3 is a waveform diagram showing electrical signals at various locations in the system in a dry condition; and FIG. 4 is a waveform diagram similar to that of FIG. 3 in a moist condition.

DESCRIPTION OF THE PREFERRED EMBODIMENT

Figures 1, 2:
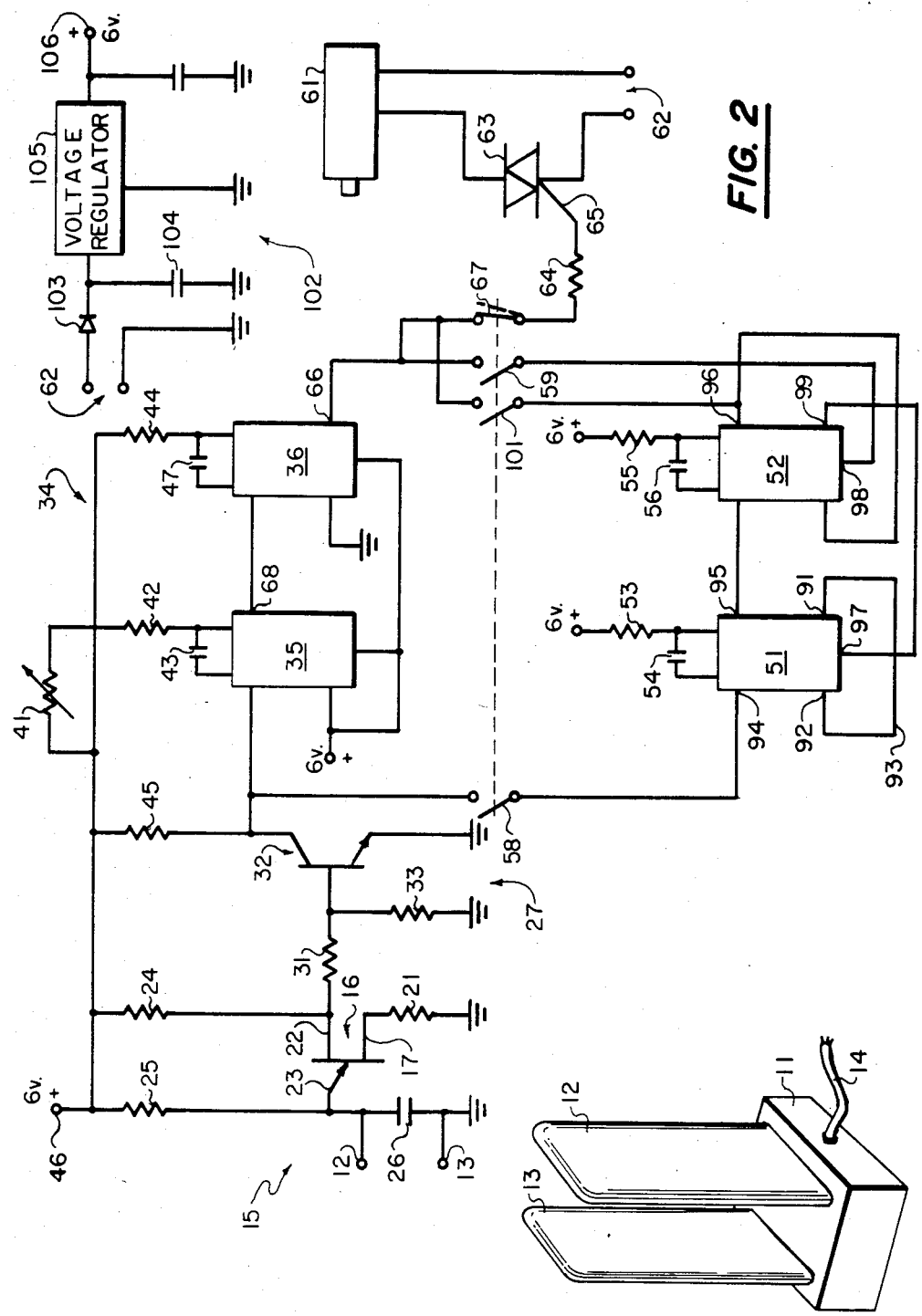
FIG. 1 is a perspective view of the structure of the invention prior to installation.
FIG. 2 is a schematic diagram of the moisture sensor system of FIG. 1.

Before describing the invention in detail, it is appropriate to make certain observations that are pertinent. The dielectric constant of air is one, while the dielectric constant of water is 80. This is a key to the invention, because soil between two capacitor plates will have a relatively low dielectric constant, closer to that of air. The amount of water between the plates directly affects the possible capacitance between them. Depending on the percentage of the space between the plates that is moist, their capacitance is significantly increased.

With reference now to the drawing, and more particularly to FIG. 1, there is shown a base member 11 from which extend parallel plates 12 and 13. The base member houses the circuitry of the invention shown in FIG. 2, including the oscillator and timing circuitry, while plates 12 and 13 comprise the sensing capacitor. The circuitry is preferably potted by a suitable epoxy within base member 11 to prevent moisture from entering the circuit area. Cable 14 extends from the base and is connected to the circuitry therein, the distal end of the wire being connected to the preexisting watering system including the solenoid and the AC power source. The specific structure of plates 12 and 13 as envisioned comprise a typical printed circuit board base with one or both sides coated with copper and then a rubber or epoxy coating over that. Alternatively, plates 12 and 13 may be rolled steel or other suitable material to function as capacitor plates.

In the schematic diagram of FIG. 2, the oscillator is referred to by reference numeral 15 and comprises unijunction transistor 16 having base 17 connected to ground through resistor 21. Base 22 is connected to emitter terminal 23 through resistors 24 and 25. The frequency of operation of oscillator 15 is governed by the capacitance between plates 12 and 13. Capacitor 26 is in parallel with the main capacitor and functions to provide a base, or dry operating frequency.

Buffer 27 is connected to oscillator 15 through resistor 31. The base of buffer transistor 32 is coupled to ground through resistor 33 and the emitter is grounded.

Timing circuit 34 comprises retriggerable monostable multivibrators 35 and 36. The circuit is calibrated by means of variable resistor 41 connected to resistor 42 and capacitor 43 comprising the RC network controlling the timing of multivibrator 35. The other end of variable resistor 41, together with resistor 44 connected to multivibrator 36 and resistor 45 connected to the collector of transistor 32, are all connected to a 6-volt power supply terminal 46. Resistors 24 and 25 are also connected in parallel to this power supply.

Solenoid 61 is the control solenoid for the lawn watering system and 24-volt AC power supply 62 is the power supply for the lawn watering system. The output of the moisture sensor of FIG. 2 is applied to triac 63 through resistor 64, the control signal being applied to gate 65 of the triac.

The portion of the circuitry which controls the time of operation of solenoid 61 is comprised of retriggerable monostable multivibrators 35 and 36, typically physically contained on a single integrated circuit element. This timing means functions as a pulse period comparator as will become evident hereinbelow. The time-out period of multivibrator 35, governed by resistor 42, variable resistor 41 and capacitor 43, is in the general range of the period of the oscillator output frequency. The frequency of the oscillator, being variable, will at times have a period which is greater than the time-out period of multivibrator 35 and at times its period will be less than the time-out period of the multivibrator. The time-out period of multivibrator 36 is governed by resistor 44 and capacitor 47. These elements typically have a much higher value than do the corresponding elements of multivibrator 35 so that the time-out period of this second multivibrator is substantially longer, even as much as a second order of magnitude longer, than that of the first multivibrator.

The timing of the circuit when the sensed material is dry and wet is shown respectively in the waveforms of FIGS. 3 and 4. When the lawn is dry, the capacitance between plates 12 and 13 decreases and the frequency of oscillator 15 is relatively high. The pulsed output of the oscillator is shown by curve 71 in FIG. 3. Buffer 27 converts the relatively small negative pulses from the oscillator to larger positive going pulses 72.

The time-out period of multivibrator 35 is shown by dotted lines 74 to be somewhat longer than the period between the oscillator output pulses. Because the multivibrator is of the monostable, retriggerable type, as soon as the first output pulse 72 from buffer 27 is applied to the multivibrator, it is triggered to the ON state as indicated by curves 73 and 75, and is continually retriggered by pulses 72 so that it stays in the ON state. Assuming the time-out period from each trigger pulse to be as shown by dotted lines 74, each succeeding time-out of multivibrator 35 fails to materialize because there has been a pulse from the buffer which retriggers the multivibrator.

The output terminal 66 of multivibrator 36 is normally coupled to gate 65 of the triac through normally closed switch 67 and resistor 64. When multivibrator 35 is triggered ON as indicated by positive going curve 75 coincident with the first pulse 72, multivibrator 36 is unaffected, as indicated by zero voltage level line 81. Multivibrator 36 requires a negative going input to trigger. Therefore, it remains inactive under the conditions of FIG. 3 and the output at pin 66 remains high, maintaining the triac in an ON condition. While the output of terminal 66 remains in a high or ON state as indicated by line 81, the triac is turned on, solenoid 61 is energized and the watering system continues to function.

When the water in the soil reaches a higher level at the location of plates 12 and 13, the output frequency of oscillator 15 will eventually reach a point where the period between pulses is greater than the time-out period of multivibrator 35. This is indicated in FIG. 4 where oscillator pulses 82 and corresponding buffer pulses 83 have a period greater than the time-out period of multivibrator 35 as indicated by negative going pulses 84. Thus when the frequency reaches this lower level, multivibrator 35 effectively has a pulsing output on terminal 68 which is coupled to multivibrator 36. As indicated by negative going curve 85, as soon as multivibrator 35 is triggered to emit negative going pulse 84, multivibrator 36 is triggered to provide a negative output on terminal 66. Because multivibrator 36 is retriggerable, each pulse 84 of multivibrator 35 will retrigger multivibrator 36 thereby maintaining the negative output at terminal 66 as indicated by a line 86 of multivibrator 36. This negative output ensures that triac 63 is turned off and the water applied to the soil ceases or stays off.

The circuit of FIG. 2 has a fail-safe feature in that if the circuit fails, the output at terminal 66 of multivibrator 36, since the multivibrator is not being triggered, will remain high as shown in FIG. 3. This ensures that the water flow will commence and remain on until someone realizes there is a failure or a malfunction and takes the necessary corrective action. It has been determined that this fail-safe mode is better than if the system failed off. In the latter case there would be nothing to call attention to the failure until the lawn was very dry and possibly badly damaged. Excess running water on the other hand, is more visible, and too wet is normally a better situation than too dry.

The lower portion of the circuit of FIG. 2 provides an alternative timing circuit to that of the combination of multivibrators 35 and 36. It is the purpose of the circuit with multivibrators 51 and 52 to alternate periods of watering with periods of non-watering. The purpose is for additional water conservation. If, for example, the soil with which the moisture sensor of this invention is working is less permeable than ideal, it is possible that watering until the sensor detects that the soil is adequately moist could result in undesired runoff and substantial waste of water. By specific example, the timing provided by multivibrators 51 and 52, when the soil is dry, provides two minutes of watering followed by five minutes where the watering system is turned off. The cycle is repeated until the sensor determines that there is adequate moisture. Of course the actual as well as the relative timing of these multivibrators is arbitrary and can be set as desired.

Note that the input to multivibrator 35 and the output from multivibrator 36 are connectable through switches 58 and 59 to the chip containing the two multivibrators 51 and 52. The connection of terminals 91 and 92 by means of line 93 makes multivibrator 51 non-retriggerable. Since multivibrator 51 is not retriggerable, when a pulse from buffer 27 is applied to terminal 94, the multivibrator is set and stays set until it times out, for example, five minutes. The timing out is determined by resistor 53 and capacitor 54 as described with respect to the other multivibrators. Because there is always a train of pulses coming from buffer 27 due to the action of oscillator 15, multivibrator 51 is continuously being triggered, whether the soil is wet or dry. As soon as a five minute period has been timed out, the multivibrator is again triggered by the next pulse from the buffer and remains on for another five-minute period.

If the soil is relatively dry, the output from multivibrator 36 through terminal 66 is high as indicated by line 81 in FIG. 3. This signal is applied to terminal 98 thereby enabling multivibrator 52 to function in its normal manner. When the output from terminal 95 of multivibrator 51 drops so that multivibrator times out, multivibrator 52 is turned on. The output from terminal 96 of multivibrator 52 is coupled to gate 65 of the triac through switch 101. When terminal 96 is high, terminal 99 is low, and vice versa. At this time triac 63 and solenoid 61 are enabled and the low output from terminal 99 is coupled to terminal 97 of multivibrator 51 to disable that element. Assuming the time-out period of the second multivibrator to be two minutes, after two minutes, multivibrator 52 times out and releases multivibrator 51 to be triggered again by the next pulse from buffer 27. When multivibrator 51 is again triggered, the output from terminal 95 disables multivibrator 52 until the first multivibrator is again timed out and a negative going pulse at terminal 95 enables the second multivibrator.

When the soil is wet, the low output from multivibrator 36 through terminal 66 is applied to terminal 98 of multivibrator 52, effectively locking out that multivibrator, thereby preventing the triac from firing. Even though multivibrator 51 is being timed out at five minute intervals, as long as multivibrator 52 is locked out, there is no signal applied to gate 65 of the triac to turn on solenoid 61.

Only one of these two multivibrators can ever be on at a time. Stated another way, multivibrator 51 starts multivibrator 52, while multivibrator 52 disables multivibrator 51 until multivibrator 52 is timed out. Thus as long as the sensor determines that the lawn needs water, the relatively high frequency of oscillator 15 will continue to operate the watering system through solenoid 61 in cycles of two minutes on, spaced by five minutes off. Because of this on/off relationship between these two multivibrators, element 52 need not be specifically configured as retriggerable or non-retriggerable.

The timing circuitry of multivibrators 51 and 52 is shown as an addition and alternative to the system using only multivibrators 35 and 36. The latter two multivibrators are not removed from the system when elements 51 and 52 are employed. As presently envisioned, the system would either be permanently constructed with multivibrators 51 and 52 included, or they would not be in the circuit at all. However, the concept of switching one operation to the other could be employed, using electronic switches, if desired.

As stated previously, variable resistor 41 is used for calibrating purposes and sets the trip point of the system. If the resistance is set larger, the frequency for turning off the watering system goes lower because multivibrator 35 has a longer time-out period and therefore the off signal will occur when the moisture is at a higher level. If the resistance of resistor 41 is made smaller, the moisture sensor will turn the watering system off at a lower moisture content in the soil.

Note that the set point determined by resistor 41 provides the same moisture level to turn the system off as to turn it on. The reason that the system is not constantly going on and off is that the plates 12 and 13 of the sensor are buried approximately six inches deep in the soil. As the soil surface starts to dry out, it takes some time for that relative dryness to creep down to the vicinity of the plates so that the frequency of oscillator 15 can increase sufficiently to trip the solenoid to commence watering. In this way, the depth that the moisture sensor is buried effectively controls the amount of moisture in the soil. If it is determined that the system is running too dry, the sensor can be buried deeper. Conversely, if the lawn tends to be too wet, the sensor should be buried more shallowly so that it can more quickly detect moisture in the soil before it becomes too wet.

The circuit represented by reference numeral 102 is the circuit power supply. As indicated previously, standard watering systems are provided with 24-volt AC power. The system of this invention needs something other than 24 volts AC, that being 6 volts DC. Of course, the actual DC voltage value employed by the moisture sensor is not critical and a different set of components could result in a different voltage level being needed. Diode 103 is a rectifier providing DC pulses and capacitor 104 functions as a filter. Voltage regulator 105 provides a constant 6 volts at output terminal 106, substantially independently of input.

While the system described above has been discussed as a moisture sensor for soil and soil watering systems, the principles of the invention could be employed in many situations where moisture content is an important characteristic. If the moisture sensor of this invention is used specifically for trees as opposed to lawns, it could be buried substantially deeper so that the moisture will penetrate to the deeper roots before the system turns off the watering function. Completely unrelated to providing water for plants, the system could be modified to detect some aspect of the moisture content in a human body. Many other possibilities exist, including the sensing of moisture content in concrete such as foundations or other structures, large storage containers, such as grain silos or other food stuff stored in bulk. It should also be evident that the principles of this invention could be adapted to power supplies other than 24 volts AC, and to watering or other controlled systems employing something other than a solenoid. Further, the sensor of this invention need not actuate something equivalent to a watering system. It could only actuate an indicator of the wet or dry condition being detected. In any event, the output of the system functions to indicate the moisture content condition, whether it controls a watering system, some other event, or provides only a visual indication having no other function. Further, while two plates of equal size are shown in confronting parallel arrangement, other physical arrangements for the capacitor could be employed. It is envisioned that a sufficient amount of the material of interest (soil) must be present between the capacitor plates for an exemplary sampling of ambient moisture content. For this reason, the capacitor plates are preferably about 1½ inches (3.8 cm) apart but could be closer or spaced farther as desired.

In view of the above description it is likely that modifications and improvements will occur to those skilled in the art which are within the scope of the accompanying claims.

What is claimed is:

1. A moisture sensor for detecting percentage moisture in a substance, said sensor being adapted to be coupled to indication means and comprising:

a variable frequency oscillator having a pulsed output;

plate capacitance means in said oscillator, the capacitance value thereof being responsive to the percentage of moisture between the plates of said capacitance means, the frequency of said oscillator being linearly related to the capacitance value of said capacitance means;

timing means coupled to said oscillator output, said timing means having a set point, the output of said timing means depending on the value of said set point and being adapted to be coupled to the indication means, said timing means comprising:

a first timing device having a predetermined first time-out period and comprising a retriggerable, monostable multivibrator, the output of which is constant when the period of the pulses from said oscillator is shorter than said first time-out period; and a second timing device having a predetermined second time-out period substantially longer than said first time-out period, said second timing device comprising a retriggerable, monostable multivibrator adapted to provide an enable signal to the indicating means when the period of the pulses from said oscillator is shorter than the time-out period of said first timing device;

the output of said first timing device being pulsed when the period of the pulses from said oscillator is longer than said first time-out period, whereby said second timing device is adapted to provide a constant disable signal to the indication means; and means for varying the value of said set point, said set point varying means being connected to said first timing means so as to vary said first time-out period;

said oscillator output being applied to said first timing device;

said second timing device being coupled to the output of said first timing device and being adapted to be coupled to the indication means;

whereby the moisture content at which said timing means is adapted to trigger the indication means is dependent on the value of said set point;

whereby when the moisture percentage is above a value corresponding to the value of said set point, the output of said second timing device is adapted to trigger the indication means to indicate a high level of moisture in the substance; and when the moisture percentage is below a value corresponding to the value of said set point, the output of said second timing device is adapted to trigger the indication means to indicate a low level of moisture in the substance.

2. The sensor recited in claim 1, wherein said set point varying means comprises a variable resistor.

3. The sensor recited in claim 1, and further comprising a buffer between said oscillator and said timing means, said buffer operating to condition the output pulses from said oscillator for proper functioning with said timing means.

4. The sensor recited in claim 1, wherein:

said indication means is a power supply and control element of an existing watering system for an area of soil;

said sensor further comprising:

a control system for controlling the operation of said watering system;

said control system comprising gating means coupled between the output of said timing means and the control element of the existing system;

said timing means triggers the existing system into operation depending on the moisture content in the soil, the moisture content at which said timing means functions to trigger the watering system being dependent on the value of said set point.

5. The sensor recited in claim 4, wherein:

said second timing device is coupled between the output of said first timing device and said gating means, the output of said second timing device disables said gating means thereby preventing the watering system from functioning to supply water when the moisture percentage in the soil is above the value corresponding to the value of said set point; and the output of said second timing device enables said gating means, thereby turning on the water supply function of the existing system when the moisture percentage is below a value corresponding to the value of said set point.

6. The sensor recited in claim 4, wherein said gating means comprises a triac.

7. A moisture sensor for detecting percentage moisture in a substance, said sensor being adapted to be coupled to indication means and comprising:

a variable frequency oscillator having a pulsed output;

plate capacitance means in said oscillator, the capacitance value thereof being responsive to the percentage of moisture between the plates of said capacitance means, the frequency of said oscillator being linearly related to the capacitance value of said capacitance means;

timing means coupled to said oscillator output, said timing means having a set point, the output of said timing means depending on the value of said set point and being adapted to be coupled to the indication means, said timing means comprising:

a first timing device having a predetermined first time-out period;

a second timing device having a predetermined second time-out period substantially longer than said first time-out period;

a third timing device having a predetermined third time-out period; and a fourth timing device having a predetermined fourth time-out period;

said oscillator output being applied to said first and third timing devices;

said second timing device being coupled between the output of said first timing device and said fourth timing device;

said fourth timing device being coupled to the output of said third timing device and being adapted to be coupled to the indication means;

means for varying the value of said set point, said set point varying means being connected to said first timing device so as to vary said first time-out period;

whereby the moisture content at which said timing means is adapted to trigger the indication means is dependent on the value of said set point;

whereby when the moisture percentage is above a value corresponding to the value of said set point, the output of said second timing device disables said fourth timing device, the output of said fourth timing device being adapted to disable the indication means to thereby indicate a high moisture content in the substance; and when the moisture percentage is below a value corresponding to the value of said set point, the output of said second timing device enables said fourth timing device;

the time-out period of said third timing device being different than the time-out period of said fourth timing device, said third timing device continually providing a pulsed output, said fourth timing device providing an output only upon being pulsed by the output of said third timing device, said third timing device being disabled by a signal from said fourth timing device when said fourth timing device is enabled by a signal from said second timing device.

8. The sensor recited in claim 7, wherein:

said first timing device comprises a retriggerable, monostable multivibrator;

said second timing device comprises a retriggerable, monostable multivibrator;

said third timing device comprises a non-retriggerable, monostable multivibrator; and said fourth timing device comprises a monostable multivibrator.

9. A sensor recited in claim 7, wherein said indication means is a gating means, the output of said fourth timing device disabling said gating means thereby preventing the existing system from functioning to supply water to the soil when the moisture percentage is above a value corresponding to the value of said set point, and the output of said second timing device disables said fourth timing device.

10. A moisture sensor and control system adapted to be coupled to the power supply and control elements of an existing soil watering system for a specified area, said sensor and control system comprising:

a variable frequency oscillator having a pulsed output;

plate capacitance means in said oscillator, the capacitance thereof being responsive to the percentage of moisture in the soil between the plates of said capacitance means, the frequency of said oscillator being linearly related to the capacitance value of said capacitance means;

timing means coupled to said oscillator ouput, said timing means having a set point, the ouput of said timing means depending on the value of said set point, said timing means comprising:

a first timing device having a predetermined first time-out period and comprising a retriggerable, monostable multivibrator, the output of which is constant when the period of the pulses from said oscillator is shorter than said first time-out period;

a second timing device having a predetermined second time-out period substantially longer than said first time-out period;

said oscillator output being applied to said first timing device;

means for varying the value of said set point, said set point varying means being connected to said first timing device so as to vary said first time-out period; and gating means coupled to the output of said timing means and being adapted to be coupled to the control element of the existing watering system, the output of said timing means being adapted to function to trigger the operation of the existing watering system;

said second timing device being coupled between the output of said first timing device and said gating means, said second timing device comprising a retriggerable, monostable multivibrator providing an enable signal to said gating means when the period of said pulses from said oscillator is shorter than the time-out period of said first timing device;

the output of said first timing device is pulsed when the period of the pulses from said oscillator is longer than said first said time-out period, whereby said second timing device provides a constant disable signal to said gating means;

whereby the moisture content at which said timing means is adapted to trigger the existing watering system into operation is dependent on the value of said set point;

whereby when the moisture percentage is above a value corresponding to the value of said set point, the output of said second timing device disables said gating means thereby being adapted to prevent the existing watering system from functioning to supply water to the soil; and when the moisture percentage is below a value corresponding to the value of said set point, the output of said second timing device enables said gating means thereby being adapted to turn on the water supply function of the existing watering system.

11. The system recited in claim 10, wherein said set point varying means comprises a variable resistor.

12. The system recited in claim 10, wherein said gating means comprises a triac.

13. The system recited in claim 10, and further comprising a buffer between said oscillator and said timing means, said buffer operating to condition the output pulses from said oscillator for proper functioning with said timing means.

14. The system recited in claim 10, wherein said timing means is configured to function in a fail-safe manner in that a circuit failure in said system results in the existing watering system being turned on to provide visual indication.

15. A moisture sensor and control system adapted to be coupled to the power supply and control elements of an existing soil watering system for a specified area, said sensor and control system comprising:

a variable frequency oscillator having a pulsed output;

a plate capacitance means in said oscillator, the capacitance thereof being responsive to the percentage of moisture in the soil between the plates of said capacitance means, the frequency of said oscillator being linearly related to the capacitance value of said capacitance means;

timing means coupled to said oscillator output, said timing means having a set point, the output of said timing means depending on the value of said set point, wherein said timing means comprises:

a first timing device having a predetermined first time-out period;

a second timing device having a predetermined second time-out period substantially longer than said first time-out period;

a third timing device having a predetermined third time-out period; and a fourth timing device having a predetermined fourth time-out period;

means for varying the value of said set point, said set point varying means being connected to said first timing device so as to vary said first time-out period;

said oscillator output being applied to said first and third timing devices;

said second timing device being coupled between the output of said first timing device and said fourth timing device;

gating means coupled to the output of said timing means and being adapted to be coupled to the control element of the existing watering system, the output of said timing means functioning to trigger the operation of the existing watering system;

said fourth timing device being coupled between the output of said third timing device and gating means;

whereby the moisture content at which said timing means is adapted to trigger the existing watering system into operation is dependent on the value of said set point;

whereby when the moisture percentage is above a value corresponding to the value of said set point, the output of said second timing device disables said fourth timing device, the output of said fourth timing device disables said gating means thereby being adapted to prevent the existing watering system from functioning to supply water to the soil; and when the moisture percentage is below a value corresponding to the value of said set point, the output of said second timing device enables said fourth timing device;

the time-out period of said third timing device is different than the time-out period of said fourth timing device, said third timing device continually providing a pulsed output, said fourth timing device providing an output only upon being pulsed by the output of said third timing device, said third timing device being disabled by a signal from said fourth timing device when said fourth timing device is enabled by a signal from said second timing device.

16. The system recited in claim 15 wherein:

said first timing device comprises a retriggerable, monostable multivibrator;

said second timing device comprises a retriggerable, monostable multivibrator;

said third timing device comprises a non-retriggerable, monostable multivibrator; and said fourth timing device comprises a monostable multivibrator.

* * * * *